(12) United States Patent  
Pews

(10) Patent No.: US 6,670,474 B2
(45) Date of Patent: Dec. 30, 2003

(54) EPOXIDE DERIVATIVES OF ALLYLARYLPHENOLS

(76) Inventor: R. Garth Pews, 4830 Osprey Dr., S., Apt. 902, St. Petersburg, FL (US) 33711

( * ) Notice: Subject to any disclaimer, the term of this patent is extended or adjusted under 35 U.S.C. 154(b) by 0 days.

(21) Appl. No.: 10/095,353

(22) Filed: Mar. 11, 2002

(65) Prior Publication Data

US 2002/0151731 A1 Oct. 17, 2002

Related U.S. Application Data

(60) Provisional application No. 60/284,325, filed on Apr. 17, 2001.

(51) Int. Cl.$^7$ ................. C07D 303/08; C07D 405/14
(52) U.S. Cl. ................. 544/238; 549/554; 549/563
(58) Field of Search ................. 544/238; 549/219, 549/554, 563

(56) References Cited

U.S. PATENT DOCUMENTS 56,806 A  * 10/1866 Phillips et al.

OTHER PUBLICATIONS

Talyanker et al., Zhurnal Obshchei Khimii (1966), 36(8), pp. 1473–1474.*
Kourtides et al., Annual Pacific Tech. Conf., [Tech Papers] (Soc of Plastics Engineers) (1979), 4, pp.51–54.*

* cited by examiner

Primary Examiner—Taofiq Solola
(74) Attorney, Agent, or Firm—Bernd W. Sandt

(57) ABSTRACT

The present invention relates to novel epoxides having the formulas

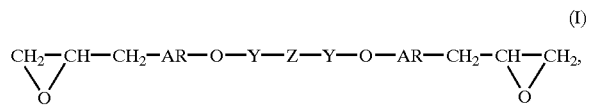

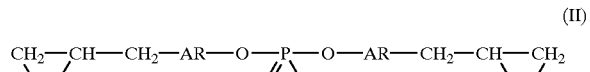

and

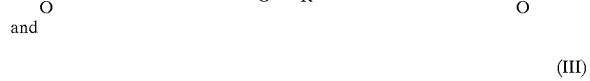

where Y is a CO, $CO_2$ or $SO_2$, AR is the same or different divalent unsubstituted or substituted aromatic, halogen-substituted aromatic or cyano-substituted aromatic hydrocarbon radical having from 6 to 20 carbon atoms, Z is a divalent hydrocarbon or ether radical having from 1 to 20 carbon atoms, including Y-Z-Y being CO, and R* is an alkyl, aryl, arylalkyl, alkoxy, aryloxy or arylalkoxy radical having from 0–20 carbon atoms. The epoxides of the present invention are useful in the formation of epoxy resins.

24 Claims, No Drawings

EPOXIDE DERIVATIVES OF ALLYLARYLPHENOLS

This application claims the benefit of provisional application 60/284,325 filed Apr. 17, 2001.

BACKGROUND OF THE INVENTION

The epoxy intermediates and resins industry (Encyclopedia of Chemical Technology, Volume 9. Fourth Edition. John Wiley & Sons Page 730) is a multibillion dollar business that is based on the following technology that involves no less than ten chemical reactions. This application is a continuation-in-part of Ser. No. 60/284,325 filed Apr. 17, 2001.

Benzene+propylene→isopropylbenzene
Isopropylbenzene→cumene hydroperoxide
Cumene hydroperoxide→phenol+acetone.
Phenol+acetone→"Bis-A" or Phenol+formaldehyde→"Bis-F"
Propylene+chlorine→allyl chloride
Allyl chloride+sodium hydroxide+chlorine→propylene chlorohydrins
Propylene chlorohydrins+sodium hydroxide→epichlorohydrin
Bis-A+epichlorohydrin+NaOH→"Bis-A glycidol ether"
Bis-A glycidol ether+Bis-A→epoxy resin
Sodium chloride+water→chlorine+sodium hydroxide.

Several aspects of the above reaction sequence have negative process implications with regards to yields, chlorinated byproducts, hydraulic load and biological hazards. These include but are not limited to the following: (a) benzene is a known carcinogen, (b) Bis-A is an endocrine disrupter (mimics estrogen), (c) chlorination of propylene to allyl chloride (step 5) and the addition of hypochlorous acid (step 6) yield higher chlorinated byproducts resulting in ~⅓ pounds of chlorinated waste per pound of epichlorohydrin. In addition, the process requires a chlor-alkali facility, hence a local source of salt and huge volumes of water. The products and processes of the present invention ameliorate if not eliminate some of the disadvantages of prior art epoxy products and processes.

BRIEF DESCRIPTION OF THE INVENTION

The present invention relates to the preparation of bis-esters and ethers of allylarylphenols and the epoxidation of the allyl moiety to provide novel bis-epoxide ester and ether intermediates useful in the preparation of epoxy resins. The epoxy ethers and esters of carboxylic, carbonic, phosphoric and sulfonic acids of the present invention are represented by the following formulas:

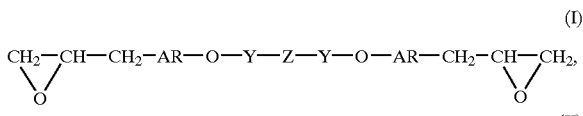

(I)

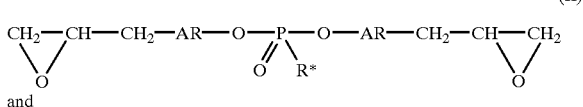

(II)

and

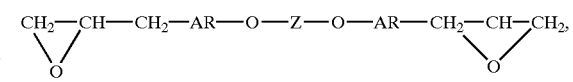

(III)

where Y is a CO, $CO_2$ or $SO_2$, AR is a divalent unsubstituted or substituted aromatic, halogen-substituted aromatic or cyano-substituted aromatic hydrocarbon radical having from 6 to 20 carbon atoms, Z is a divalent hydrocarbon or ether radical having from 1 to 20 carbon atoms, including YZY being CO, and R* is an alkyl, aryl, arylalkyl, alkoxy, aryloxy or arylalkoxy radical having from 0–20 carbon atoms.

Preferred aromatic "AR" radicals include divalent benzene, naphthalene, toluene, chlorobenzene, cyanobenzene, xylene and ethylbenzene radicals. Preferred hydrocarbon "Z" radicals include divalent aliphatic radicals such as divalent methane, ethane, butane, and cyclohexane, divalent aromatic radicals such as divalent benzene, toluene, xylene and ethylbenzene radicals. Preferred ether "Z" radicals include such divalent radicals as divalent ethoxyethane, ethoxypropane, propoxypropane, butoxyethane methoxybenzene, and ethoxybenzene. Preferred R* radicals include methyl, ethyl, propyl, isobutyl, cyclohexyl, phenyl, benzyl, naphthyl, toluyl and xylyl.

DETAILED DESCRIPTION OF THE INVENTION

The preparation of allylarylphenols used in the present invention is well documented in the chemical literature and is illustrated for 2-allylphenol. The formation of the ether and the rearrangement are carried out in the same reactor.

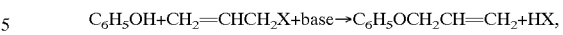

where X is Cl, Br, acetate, tosylate, or similar leaving group.

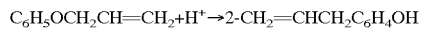

The preparation of bis-aromatic disulfonyl chlorides is also well-documented in the literature and is achieved via the sulfonation or chlorosulfonation of aromatic compounds ("Friedel Crafts and Related Reactions", Volume 3, Part 2, page 1355, Interscience Publishers, 1964, C. M. Suter, "Organic Chemistry of Sulfur Compounds", Chapter 3 John Wiley and Sons, 1944, and "Organic Functional Group Preparations", S. R. Sandler and W. Karo, Academic Press 1968, page 506). The reactions are preferably carried out in 1,2-dichloroethane as solvent. If higher reaction temperatures are required for the bis sulfonation, the reaction may be performed without a solvent. Reaction of the aromatic disulfonyl chloride with two equivalents of the allylarylphenol in the presence of an acid acceptor gives the desired bis-sulfonate ester which is converted to the desired bis-epoxide in essentially quantitative yield with standard utilized oxidants e.g., peracetic acid, 3-chloroperbenzoic acid, hydrogen peroxide, t-butyl hydroperoxide etc. The latter two reagents require a metal catalyst ("Oxidations in Organic Chemistry", M. Hudlicky, ACS Monograph 186, page 60. American Chemical Society).

The allylarylphenyl ester of dicarboxylic acids are conveniently prepared from the reaction of the dicarboxylic acid dichloride with the allylarylphenol in an inert solvent such as toluene, dichloromethane, 1,2-dichloromethane etc. in the presence of a hydrogen acceptor such as pyridine, triethylamine, etc. The use of the hydrogen acceptor can be eliminated by simply refluxing the phenol and acid chloride in a higher boiling solvent to effect displacement of the anhydrous HCl that may be recovered for alternate uses. If a lower dialkyl ester of the dicarboxylic acid is available, ester exchange of the allylarylphenol in the presence of a transesterification catalyst can serve as an alternative route to the bis-aryl ester ("Encyclopedia of Chemical Technology", Volume 9. Fourth Edition, John Wiley & Sons, page 755, "Survey of Synthesis", Calvin Buehler and D. E Pearson, Wiley Interscience 1970, page 101 and "Preparation of Esters using Polyphosphate Ester", J. H. Adams, J. G. Paul and J. R. Lewis, Synthesis, 429–30, 1979). The oxidation methods are identical as described above for the sulfate esters.

In the manner described for the preparation of allylphenyl esters from dicarboxylic acid dichlorides, the allylphenyl esters of dicarbonic acids are prepared from the corresponding bis-chloroformates with two equivalents of allylphenol. Similarly a carbonic acid ester, is prepared from two equivalents of allylphenol and phosgene.

The allylaryl esters of the phosphoric and phosphonic acids are readily prepared from the acid dichlorides since phosphorus oxychloride, $POCl_3$, is the basic phosphorus precursor ("Organophosphorus Compounds", G. M. Kosolapoff, John Wiley, 1950). Thus, utilization of an inert solvent and an acid acceptor as described above for the carboxylic acids gives high yields of the desired allylaryl esters that are then oxidized to the bis-epoxides as described above.

The allylaryl ethers are prepared by displacement reactions of the desired dichloride with either the allylaryl phenoxide anion or displacement by the 2,3-epoxypropylphenoxide anion. For substrates that require higher temperatures to carry out the displacement such as 4-chlorophenyl sulfone, the preferred anion is the 2,3-epoxypropylphenoxide. With the allylaryl phenoxide, displacement occurs but the 2,3-olefinic bond undergoes thermal isomerization to the 1,2-olefin. With the more reactive olefins, such as 1,4-dichlorobutane and 3,6-dichloropyridazine, olefin isomerization is not a problem. For unreactive aryl halides, reaction conditions for the Ullman reaction ether synthesis is required. Within the scope of the present invention, optimum reaction conditions can be obtained in a routine manner.

The following are examples of allylarylphenols that may be reacted with either derivatives of organic acids or dihalo compounds to form the compounds of this invention: 2-allylphenol, 2-allyl-6-methylphenol, 4-allyl-2,6-dimethylphenol, 2-allyl-4-dodecylphenol, 2-allyl-4-methoxyphenol, 2-allyl-4-phenoxyphenol, 2-allyl-4-cyclohexylphenol, 3-allyl-4-hydroxy ethyl benzoate, 2-allyl-4-chlorophenol, 2-allyl-4-cyanophenol, 2-allyl-4-benzylphenol, 2-allyl-4-chloromethylphenol, 1-allyl-2-naphthol, and 2-allyl-4-phenylphenol.

The following are examples of the disulfonic acid compounds that can be employed to prepare the diepoxides of the present invention: benzene-1,3-disulfonyl chloride, naphalene-2,6-disulfonyl chloride, phenyl ether-1,4-disulfonyl chloride, 4,4*biphenyldisulfonyl chloride, 2,5-dimethylbenzene-1,3-disulfonyl chloride, 4-octylbenzene-1,3-disulfonyl chloride, 4-methoxybenzene-1,3-disulfonyl chloride, 4-chlorobenzene-1,3-disulfonyl chloride, 4-carboethoxy-1,3-disulfonyl chloride 3,5-pyridinedisulfonyl chloride, 3,5-pyridine-N-oxide disulfonyl chloride, and 2,5-thiophenedisulfonyl chloride.

The following are examples of the dicarboxylic acid compounds which can be employed in the preparation of the novel epoxides of the present invention: terephtholyl chloride, iso-phtholyl chloride, succinoyl choride, adipoyl chloride, 1,4-cyclohexane carboxylic acid dichloride, dimethyl terephthalate, diethyl succinate, 4,4*-biphenyl dicarboxylic acid dichloride, malonyl chlorde, oxaloyl chloride and 3,5-pyridine-dicarboxylic acid dichloride.

The following are examples of the starting materials which can be employed in the formation of the novel bis-epoxide ethers of the present invention: 1,2-dichloroethane, 1,4-dichlorobutane, 1,4-dichloro-2-butene, 1,12-dichlorododecane, 1,4-dichlorocyclohexane, 4-chlorophenyl sulfone, 4-(2-chloroethoxyphenyl)sulfone, 4,4*-dichlorobenzophenone, 2,6-difluorobenzonitrile, 2,4-dichloroacetophenone, 2,4-dichlorotoluene, 2,4-dichloro-1-methyl naphthoate, 2,6-dichloropyridine-N oxide and chlorinated polyethylene glycols having the formula $ClCH_2CH_2(OCH_2CH_2)_xCl$ where x is a number from 1 to 10.

The condensation of the bis-epoxides of this invention with diphenols, e.g., bisphenol-A, bisphenol-F, 4-hydroxyphenyl sulfone, 4,4*-dihydroxybenzophenone, 4,4*-dihydroxybiphenyl and 1,4-(4-hydroxyphenyl)butane, with dicarboxylic acids, e.g., isophthalic acid, succinic acid and cyclohexane dicarboxylic acid, with aminophenols, e.g., 4-aminophenol, 4-amino-4*-hydroxyphenyl ether, and 4-amino-4*-hydroxybiphenyl, with hydroxy carboxylic acids, e.g., 4-hydroxybenzoic acid and 6-hydroxy-6-hydroxy-2-naphthoic acid, with amino acids, e.g., 4-aminobenzoic acid, and 4-aminophenoxybenzoic acid, with diamines, e.g., 4,4*-diaminophenyl ether 1,3-diamonobenzene and 1,3-diamonipropane or with disulfonamides, e.g., 1,3-benzenedisulfonice acid:bis-N-methyl amide results in new and valuable epoxy resins for protective coatings, structural composites, electrical laminates and adhesives. The chemistry provides the opportunity to manufacture resins with fewer chemical transformations, less capital and a reduction in the waste load associated with the Bis-A/epichlorohydrin technology. The resins can be obtained from the bis-epoxides using condensation procedures established in the art. An example of a resin synthesis from readily available starting materials using the epoxide route of the present invention that requires only six chemical transformation is outlined below:

1. toluene→phenol (T. Shikada et al, J. Chem. Soc., Chem. Commun., 1994)
2. propylene→allyl acetate
3. phenol+allyl acetate→2-allylphenol
4. 2-allylphenol +isophthalic acid→diester
5. diester+$H_2O_2$→diepoxide
6. diepoxide+succinic acid→epoxy resin The following examples further illustrate novel epoxides of the present invention:

EXAMPLE 1

Preparation of 2,5-Dimethyl-1,3-Benzenedisulfonic Acid: Bis-[2-(2,3-Epoxypropyl)]Phenyl Ester.

1,4-Dimethylbenzene (10.6 g, 0.1 mol) was added dropwise to chlorosulfonic acid (60 g, 0.51 mol ) at room temperature with stirring. After the addition was complete, the reaction mixture was heated to ~100C for 1 hr, cooled to room temperature and poured onto ice-water-1,2-dichloromethane mixture with stirring. The organic layer was separated, washed with water (2x), dried over anhydrous $MgSO_4$ and the solvent evaporated to give 2,5-dimethyl-1,3-benzenedisulfonyl chloride, 26 g (86%) as a viscous liquid that solidified on standing, mp 24–27° C. Reported 25–27C. (C. M. Suter, Organic Chemistry of Sulfur Compounds, Chapter 3).

The disulfonyl chloride (20 g, 0.066 mol) and 2-allylphenol (17.70 g, 0.132 mol) were diluted with toluene (200 ml) and added to a 500 ml 3-necked round bottom flask equipped with a magnetic stirrer, condenser, and thermometer. Triethylamine (17 ml, 0.132 mol) was added dropwise and the mixture was stirred and refluxed for 2 hr. After cooling, the precipitated triethylamine hydrochloride was removed by filtration and the toluene evaporated in vacuo to give 30.2 g (94%) of the desired 2,5-dimethyl-1,3-benzenedisulfonic acid bis-(2-allylphenyl ester). Recrystallization from ethyl acetate-methanol gave product mp 76–78° C. MS m/z 498 (M+ calcd for $C_{26}H_{26}O_6S_2$=498). H NMR (300 MHz, $CDCl_3$) d 2.44 (s, 3, $CH_3$), 3.40–3.50 (m, 4, $CH_2$), 5.03–5.13 (m, 4, $CH_2$ vinyl), 5.81–6.00 (m, 2, CH vinyl), 6.88 (d, 2, aromatic), 7.09–7.37 (m, 6, aromatic), 8.09 (s, 2, aromatic).

The above diolefin (2.0 g) was dissolved in dichloromethane along with m-chloroperbenzoic acid (3.0 g, ~70%) and the solution stirred overnight at room temperature to form the diepoxide. The dichloromethane solution was washed with aqueous $Na_2CO_3$, aqueous $Na_2SO_3$ and water, dried over anhydrous $MgSO_4$ and the solvent evaporated. Recrystallization from methanol gave product mp 90–92C. Utilization of peracetic acid for 72 hr gave identical results. H NMR (300 MHz, $CDCl_3$). d 2.44 (s, 3, $CH_3$), 2.60–2.73 (m, 2, $CH_2$ epoxypropyl), 2.73–2.99 (m, 4, $CH_2$ epoxypropyl), 3.06–3.15 (m, 2, $CH_2$ epoxypropyl), 3.16–3.25 (m, 2, CH epoxypropyl), 3.25 (s, 3, $CH_3$), 6.79 (d, 2, aromatic), 7.09–7.37 (m, 6, aromatic), 8.09 (s, 2, aromatic).

EXAMPLE 2
Preparation of 1,3-Benzenedisulfonic Acid: Bis-[2-(2,3-Epoxypropyl)]Phenyl Ester The diolefinic precursor, 1,3-benzenedisulfonic acid bis-(2-allyl) phenyl ester, was prepared from 1,3-benzenedisulfonyl chloride and 2-allylphenol as described in Example 1. The product was a viscous liquid. MS m/z 470 (M+ calcd for $C_{24}H_{22}O_6S_2$=470). H NMR (300 MHz, $CDCl_3$) d 3.22–3.28 (d, 4, $CH_2$), 4.94–5.09 (m, 4, $CH_2$ vinyl), 5.68–5.91 (m, 4, CH vinyl), 6.97–7.03 (d, 2, aromatic), 7.12–7.25 (m, 6, aromatic), 7.72–8.82 (m, 4, aromatic).

Epoxidation of the above diolefin with 3-chloroperbenzoic acid using the procedures of Example 1 gave the desired diepoxide as a viscous oil. H NMR (300 MHz, $CDCl_3$) d 2.48–2.51 (m, 2, $CH_2$ epoxypropyl), 2.66–2.79 (m, 4, $CH_2$ epoxypropyl), 2.87–3.00 (m, 2, $CH_2$ epoxypropyl), 3.10–3.16 (m, 2, CH epoxypropyl), 6.91–6.98 (m, 2, aromatic), 7.14–7.27 (m, 4, aromatic), 7.62–7.69 (m, 2, aromatic), 7.88–8.25 (m, 4, aromatic).

EXAMPLE 3
Preparation of 4,4-Biphenyldisulfonic Acid: Bis-[2-(2,3-epoxypropyl)]Phenyl ester.

The diolefinic precursor, 4,4-biphenyldisulfonic acid: bis-(2-allyl) phenyl ester, was prepared from 4,4-biphenyl disulfonyl chloride and 2-allylphenol as described in Example 1. Recrystallization from methanol gave product, mp 88–90° C. Reported 88–900 C (C. M. Suter, Organic Chemistry of Sulfur Compounds, Chapter 3).MS m/z 548 (MHz calcd for $C_{30}H_{28}O_6S_2$=548). H NMR (300 MHz, $CDCl_3$) d 2.27 (d, 2, $CH_2$), 4.96–5.06 (m, 2, $CH_2$ vinyl), 5.72–5.91 (m, 1, CH vinyl), 7.06–7.34 (m, 4, aromatic), 7.94 (q, 4, aromatic).

Epoxidation of the above diolefin with 3-chloroperbenzoic acid gave the desired diepoxide. Recrystallization from methanol gave product mp 99–101° C. H NMR (300 MHz, $CDCl_3$) d 2.24 (m, 2, $CH_2$ epoxypropyl), 2.66–2.91 (m, 6 $CH_2$ epoxypropyl), 3.06–3.16 (m, 2, CH epoxypropyl), 7.01 (m, 1, aromatic), 7.16–7.28 (m, 2, aromatic), 7.40–7.47 (m, 1, aromatic), 7.91 (q, 4, aromatic).

EXAMPLE 4
Preparation of 4,4-Phenyl Ether Disulfonic Acid: Bis-[2-(2,3-Epoxypropyl)]Phenyl Ester.

The diolefinic precursor, 4,4-phenyl ether disulfonic acid: bis(2-allyl) phenyl ester, was prepared from 4,4-phenyl ether disulfonyl chloride and 2-allylphenol as described in Example 1. The diolefin was a viscous oil. MS m/z 564 (M+ calcd for $C_{30}H_{26}O7S_2$=564). H NMR (300 MHz, $CDCl_3$) d 3.18–3.27 (m, 2, $CH_2$), 5.00–5.18 (m, 2, $CH_2$ vinyl), 5.78–5.94 (m, 1, CH vinyl), 7.06–7.59 (m, 4, aromatic), 7.66 (q, 4 aromatic).

Epoxidation of the above diolefin with 3-chloroperbenzoic acid gave the desired diepoxide as a viscous oil. H NMR (300 MHz, $CDCl_3$) d 2.56–2.60 (m, 2, $CH_2$ epoxypropyl), 2.66–2.91 (m, 6, $CH_2$ epoxypropyl), 3.06–3.15 (m, 2, CH epoxypropyl), 7.07–7.69 (m, 4, aromatic), 7.66 (q, 4, aromatic).

EXAMPLE 5
Preparation of 2,6-Napthalenedisulfonic Acid: Bis-[2-(2,3-Epoxypropyl)]Phenyl Ester.

The diolefinic precursor, 2,6-napthalenedisulfonic acid-bis-(2-allyl) phenyl ester was prepared from 2,6-napthalenedisulfonyl dichloride as described in Example 1. The diolefin, after recrystallization from hexane-dichloromethane, had mp 138–141° C. MS m/z 520 (m+ cacld for $C_{28}H_{24}O_6 S_2$=520). H NMR (300 MHz, $CDCl_3$) d 3.29 (d, 2, $CH_2$), 4.94–5.03 (m, 2, $CH_2$ vinyl), 5,69–5.88 (m, 1, CH vinyl), 7.04–7.23 (m, 4, aromatic), 8.07–8.43 (m, 3, aromatic).

Epoxidation of the diolefin with 3-chloroperbenzoic acid gave the desired diepoxide. After recrystallization from methanol, the product had mp 135–137° C. H NMR (300 MHz, $CDCl_3$) d 2.48–2.51 (m, 2, $CH_2$ epoxypropyl), 2.66–2.79 (m, 2, $CH_2$ epoxypropyl), 2.81–2.90 (m, 4, $CH_2$ epoxypropyl, 3.09–3.21 (m, 2, CH epoxypropyl), 7.09–7.46 (m, 6, aromatic), 8.06–8.37(m, 6, aromatic).

EXAMPLE 6
Preparation of Bis 1,4-[2-(2,3-Epoxypropyl)Phenoxy] Butane

Powdered sodium hydroxide (4.0 g, 0.1 mol) was dissolved with heating ~50C in dimethyl sulfoxide (50 ml). 2-Allylphenol (13.4 g, 0.1 mol) was added to the dimethyl sulfoxide solution followed by the 1,4-dichlorobutane (6.35 g, 0.05 mol) and the mixture was heated to 80C for 5 hr. After cooling, the reaction mixture was diluted with water and the product isolated by extraction with 1,2-dichloromethane. Filtration through a small amount of silica gel and evaporation of solvent in vacuo gave 13.1 g (82%) of a colorless oil, bis-1,4-(2-allylphenoxy) butane that crystallized on standing, mp 38–40C. MS m/z 322 (M+cacld for $C_{22}H_{26}O_2$=322). H MNR (300 MHz, $CDCl_3$) d 2.08 (d, 2, $CH_2$), 3.50 (d, 2, $CH_2$), 4.07–4.21 (m, 2, $OCH_2$), 5.03–5.14 (m, 2, $CH_2$ vinyl), 6.00–6.15 (m, 1, vinyl CH), 6.90–7.03 (m, 2, aromatic), 7.20–7.30 (m, 2, aromatic). The diolefin (2.0 g, 0.0062 mol) was added to a dichloromethane solution of 3-chloroperbenzoic acid (5.0 g, ~70% active, 50 ml) that was predried over anhydrous $MgSO_4$. The reaction mixture was stirred overnight at room temperature, washed with dilute aqueous sodium sulfite and dilute aqueous sodium carbonate, dried over anhydrous Mg $SO_4$ and the solvent evaporated in vacuo to give ~2.0 g of the diepoxide as a viscous oil. MS m/z 354 (M+ calcd for $C_{22}H_{26}O_4$=354). H NMR (300 MHz, $CDCl_3$) d 2.08 (d, 2, $CH_2$), 2.57 (d, 1, epoxypropyl $CH_2$), 2.72–2.83 (m, 2, $CH_2$ epoxypropyl), 2.83–3.03 (m, 2, epoxypropyl), 3.17–3.28 (m, 1, CH epoxypropyl), 6.78–7.04 (m, 1, aromatic), 7.20–7.35 (m, 2, aromatic).

EXAMPLE 7
Preparation of Bis-1,2-[2-(2,3-Epoxypropyl)Phenoxy] Ethane

Bis-1,2-(2-allylphenoxy)ethane was prepared from 2-allylphenol and 1,2-dichloroethane as described in Example 6 with the following exception. The crude product was distilled in vacuo to remove unreacted 2-allylphenol and the monosubstituted product prior to filtration through silica gel to give a viscous oil. MS m/z 294 (M+ calcd for $C_{20}H_{22}O_2=294$). H NMR (300 MHz, $CDCl_3$) d 3.40–3.50 (d, 2, $CH_2$), 4.40 (s, 2, $OCH_2$), 5.05–5.14 (m, 2, $CH_2$ vinyl), 5.90–6.08 (n, 1, CH vinyl), 6.91–7.09 (m, 2, aromatic), 7.18–7.32(m, 2, aromatic).

Oxidation as described in Example 6 gave the desired diepoxide as a viscous oil. MS m/z 326 (M+calcd for $C_{20}H_{22}O_4=326$). H NMR (300 MHz, $CDCl_3$) d 2.57 (d, 1, $CH_2$ epoxypropyl), 2.64–3.00 (m, 3, $CH_2$ epoxypropyl), 3.14–3.30 (m, 2, CH epoxypropyl), 4.40 (s, 2, $OCH_2$), 6.89–7.02 (m, 2, aromatic), 7.70–7.55 (m, 2,aromatic).

EXAMPLE 8
Preparation of Bis-[2-(2,3-Epoxypropyl)Phenyl]Phenyl Phosphate

Phenyl dichlorophosphate (10.5 g, 0.05 mol) was added dropwise to a solution of 2-allylphenol (13.4 g, 0.1 mol) and triethylamine (13.9 ml, 0.1 mol) in 1,2-dichloroethane (200 ml) and the mixture refluxed for 2 hr. After cooling, the precipitate, triethylamine hydrochloride was filtered, and the organic solution washed with water, dried over anhydrous Mg $SO_4$ and evaporated in vacuo. The unreacted 2-allylphenol was removed by vacuum distillation to give bis-[2-allylphenyl) phenyl phosphate as a viscous liquid. MS m/z 406 (M+calcd for $C_{24}H_{23}O_4P=406$). H NMR (300 MHZ, $CDCl_3$) d 3.46 (d, 4 $CH_2$), 4.95–5.15 (m, 4 $CH_2$ vinyl), 5.82–6.00 (m, 2 CH vinyl), 7.20–7.50 (m, 13, aromatic).

The above diolefin was converted to the desired diepoxide as described in Example 6. H NMR (300 MHz, $CDCl_3$) d 2.46 (d, 2, $CH_2$ epoxypropyl), 2.62–2.90 (m, 6, $CH_2$ epoxypropyl), 3.03–3.11 (m, 2, CH epoxypropyl), 7.21–7.51 (m, 13, aromatic).

EXAMPLE 9
Preparation of Isophthalic Acid: BIS-[2-(2,3-Epoxypropyl) Phenyl Ester]

Isophthaloyl dichloride (3.19 g, 0.0157 mol) and 2-allylphenol (4.21, 0.0313 mol) were diluted with dichloromethane (50 ml) and triethylamine (3.16 g, 0.0313 mol) added dropwise at room temperature. After stirring for 3 hr at room temperature, the amine hydrochloride was removed by filtration and the organic solution washed with water and dried over anhydrous Mg $SO_4$. Evaporation of the solvent in vacuo gave the bis-allylphenyl isophthalate as a colorless oil. MS m/z 398 (M+ calcd for $C_{26}H_{22}O_4=398$). H NMR (300 MHz, $CDCl_3$) d 3.46 (d, 2, $CH_2$), 5.01–5.12 (m, 2, $CH_2$ vinyl), 5.90–6.05 (m, 1, CH vinyl), 7.20–7.40 (m, 4, aromatic), 7.65–7.77 (m, 1, aromatic), 8.25–8.33(m, 1, aromatic), 9.05 (s, 1, aromatic).

The above diolefin was converted to the desired diepoxide as described in Example 6. H NMR (300 MHz, $CDCl_3$) d 2.5 (d, 1, $CH_2$ epoxypropyl), 2.62–2.96 (m, 3, $CH_2$ epoxypropyl), 3.22–3.30 (m, 1, CH epoxypropyl), 7.15–7.47 (m, 4, aromatic) 7.83–7.91(m, 1, aromatic), 8.25–8.33 (m, 1, aromatic), 9.05 (s, 1, aromatic).

EXAMPLE 10
Preparation of 3,6-Bis-[2-(2,3-Epoxypropyl)Phenoxy] Pyridazine

2-Allylphenol (10 g, 0.075 mol) was added to a solution of peracetic acid (30 g, 30% active) in dichloromethane (100 ml) that had been dried over anhydrous $MgSO_4$. The reaction mixture was stirred at room temperature for 48 hrs. The dichloromethane solution was washed with water, dilute aqueous $NaCO_3$, dilute aqueous $NaSO_3$ and dried over anhydrous $MgSO_4$. After evaporation of the solvent in vacuo, 2-(2,3-epoxypropyl)phenol was isolated as viscous liquid. MS m/z 150 (M+ calcd for $C_9H_{10}O_2$150). H NMR (300 MHz, $CDCL_3$) d 2.65–2.80(m, 2, $CH_2$ epoxypropyl), 2.87–2.93 (m, 1, $CH_2$ epoxypropyl), 3.10–3.21 (m, 1, $CH_2$ epoxypropyl), 3.50–3.60 (m, 1, CH epoxypropyl), 6.80–7.25 (m, 4, aromatic). 2-(2,3-Epoxypropyl)phenol (0.9 g, 0.006 mol) was added to a solution of powdered sodium hydroxide (0.24 g, 0.006 mol) in dimethylacetamide(30 ml) and the solution heated at 80C for 1 hr. The reaction mixture was diluted with water and extracted with dichloromethane, dried over anhydrous $MgSO_4$ and evaporated in vacuo to give a solid that on recrystallization from methanol gave product mp 150–152C. MS m/z 376 (M+ cacld for $C_{22}H_{20}N_2O_4=376$). H NMR (300 MHz, $CDCl_3$) d 3.62 (dq, 2, $CH_2$ epoxypropyl), 4.57 (dq, 2, $CH_2$ epoxypropyl), 5.15–5.32 (m, 1, CH epoxypropyl), 6.78–6.93 (m, 2, aromatic), 7.11 (s, 1, heteroaromatic), 7.15–7.28(m, 2, aromatic).

EXAMPLE 11
Preparation of 4-[2-(2,3-Epoxypropyl)Phenyl]Sulfone

This compound was prepared using dichlorophenyl sulfone and 2-allylphenol as described in Example 10. The compound is a viscous liquid and was purified by column chromatography utilizing silica gel. H NMR (300 MHz ,$CDCL_3$) d 3.35 (dq, 2, $CH_2$ epoxypropyl), 3.91(dq, 2, $CH_2$ epoxypropyl), 5.03–5.20 (m, 1, CH epoxypropyl), 6.84–7.03 (m, 2, aromatic), 7.22–7.35 (m, 2, aromatic), 7.75 (d, 2, aromatic).

The preparation of epoxy resins from the described epoxides of the present invention follows procedures described in the literature for the preparation of epoxy resins.

What is claimed is:
1. Diepoxide ethers of allyl phenols having the formulas:

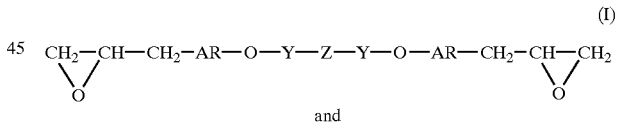

and

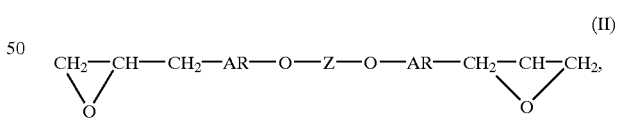

where Y is a CO, $CO_2$ or $SO_2$, AR is the same or different divalent unsubstituted or substituted aromatic, halogen-substituted aromatic or cyano-substituted aromatic hydrocarbon radical having from 6 to 20 carbon atoms, Z is a divalent hydrocarbon or ether radical having from 1 to 20 carbon atoms, and Y-Z-Y is CO.

2. The diepoxide esters of claim 1 having the formula:

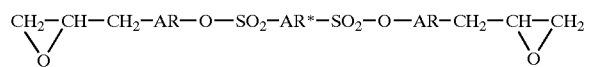

where AR* is a divalent aromatic radical of 6 to 20 carbon atoms.

3. The diepoxide esters of claim 1 having the formula:

$$CH_2\!\!-\!\!CH\!\!-\!\!CH_2\!\!-\!\!AR\!\!-\!\!CO_2\!\!-\!\!X\!\!-\!\!CO_2\!\!-\!\!AR\!\!-\!\!CH_2\!\!-\!\!CH\!\!-\!\!CH_2$$
$$\underset{O}{\diagdown\!\!\diagup}\qquad\qquad\qquad\qquad\qquad\underset{O}{\diagdown\!\!\diagup}$$

where X is arylene, alkylene or arylalkylene or alkylarylene.

4. The bis-epoxides ethers of claim 1 having the formula:

$$CH_2\!\!-\!\!CH\!\!-\!\!CH_2\!\!-\!\!AR\!\!-\!\!O\!\!-\!\!X\!\!-\!\!O\!\!-\!\!AR\!\!-\!\!CH_2\!\!-\!\!CH\!\!-\!\!CH_2$$
$$\underset{O}{\diagdown\!\!\diagup}\qquad\qquad\qquad\qquad\underset{O}{\diagdown\!\!\diagup}$$

where X is arylene, alkylene, alkylarylene or arylalkylene.

5. The diepoxide ester of claim 1 having the formula:

$$CH_2\!\!-\!\!CH\!\!-\!\!CH_2\!\!-\!\!AR\!\!-\!\!OC\!\!-\!\!X\!\!-\!\!O\!\!-\!\!CO\!\!-\!\!AR\!\!-\!\!CH_2\!\!-\!\!CH\!\!-\!\!CH_2,$$
$$\underset{O}{\diagdown\!\!\diagup}\quad\underset{O}{\|}\quad\underset{O}{\|}\quad\underset{O}{\diagdown\!\!\diagup}$$

where X is arylene, alkylene, alkylarylene or arylalkylene.

6. The diepoxide of claim 1 having the formula:

$$CH_2\!\!-\!\!CH\!\!-\!\!CH_2\!\!-\!\!AR\!\!-\!\!O\!\!-\!\!C\!\!-\!\!O\!\!-\!\!AR\!\!-\!\!CH_2\!\!-\!\!CH\!\!-\!\!CH_2.$$
$$\underset{O}{\diagdown\!\!\diagup}\qquad\underset{O}{\|}\qquad\underset{O}{\diagdown\!\!\diagup}$$

7. The diepoxide of claim 5 where the bis-carbonate is resorcinol:bis[2(2,3-epoxypropyl)phenyl]carbonate.

8. The diepoxide of claim 6 where the bis-carbonate is bis[2(2,3-epoxypropyl)phenyl]carbonate.

9. The diepoxide of claim 2 where the diester is 2,5-dimethyl-1,3-benzenedisulfonic disulfonic acid: bis-[2-(2,3-epoxypropyl)]phenyl ester.

10. The diepoxide of claim 2 where the diester is 1,3-benzenedisulfonic acid bis-[2-(2,3-epoxypropyl)]phenyl ester.

11. The compound of claim 2 where the diester is 4,4-biphenyldisulfonic acid bis-[2(2,3-epoxypropyl)]phenyl ester.

12. The diepoxide of claim 2 where the diester is 4,4-phenyl ether disulfonic acid: bis-[2-(2,3-epoxypropyl)]phenyl ester.

13. The diepoxide of claim 2 where the diester is 2,6-napthalenedisulfonic acid: bis-[2-(2,3-epoxypropyl)]phenyl ester.

14. The diepoxide of claim 3 where the diester is isophthalic acid: bis-[2-(2,3-epoxypropyl)]phenyl ester.

15. The diepoxide of claim 3 where the diester is succinic acid: bis-[2–2,3-epoxypropyl)]phenyl ester.

16. The diepoxide of claim 4 where the diether is bis-[2-(2,3-epoxypropyl)phenoxy]ethane.

17. The diepoxide of claim 4 where the ether is bis-[2-(2,3-epoxypropyl)phenoxy]butane.

18. The diepoxide of claim 4 where the ether is bis-[2-(2,3-epoxypropyl)phenoxy]pyridazine.

19. The diepoxide of claim 4 where the ether is 4-[2-(2,3-epoxypropyl)phenyl]sulfone.

20. The preparation of bis-epoxides of aryl sulfate esters of claim 2 by reacting an aryl disulfonic acid compound with an allyl compound of the formula $CH_2\!\!=\!\!CH\!\!-\!\!AR$ wherein AR is an aromatic moiety and epoxidizing the resulting diolefin.

21. The preparation of bis-epoxides of carboxylic acids esters of claim 3 by reacting a dicarboxylic acid compound with an allyl compound of the formula $CH_2\!\!=\!\!CH\!\!-\!\!CH_2\!\!-\!\!AR$ wherein AR is an aromatic moiety and epoxidizing the resulting diolefin.

22. The preparation of bis-epoxides of ethers of claim 4 by reacting a dihalo hydrocarbon with an allyl compound of the formula $CH_2\!\!=\!\!CH\!\!-\!\!CH_2\!\!-\!\!AR$ wherein AR is an aromatic moiety and epoxidizing the resulting diolefin.

23. The preparation of diepoxides of claim 5 which comprises reacting a bis-chloroformate with an allyl compound of the formula $CH_2\!\!=\!\!CH\!\!-\!\!CH_2\!\!-\!\!AR$ and epoxidizing the resulting diolefin.

24. The preparation of diepoxides of claim 6 comprising reacting phosgene and an allyl compound of the formula $CH_2\!\!=\!\!CH\!\!-\!\!CH_2\!\!-\!\!AR$ and epoxidizing the resulting diolefin.

* * * * *